(12) United States Patent
Hunter et al.

(10) Patent No.: US 7,018,610 B2
(45) Date of Patent: Mar. 28, 2006

(54) POLYMER PRECURSORS OF RADIOLABELED COMPOUNDS, AND METHODS OF MAKING AND USING THE SAME

(75) Inventors: Duncan H. Hunter, London (CA); Mustafa Janabi, Windsor (CA)

(73) Assignee: University of Western Ontario, London (CA)

( * ) Notice: Subject to any disclaimer, the term of this patent is extended or adjusted under 35 U.S.C. 154(b) by 249 days.

(21) Appl. No.: 10/091,168

(22) Filed: Mar. 4, 2002

(65) Prior Publication Data

US 2002/0182169 A1     Dec. 5, 2002

Related U.S. Application Data

(60) Provisional application No. 60/272,324, filed on Mar. 2, 2001, provisional application No. 60/280,225, filed on Mar. 30, 2001.

(51) Int. Cl.
*A61K 51/00*     (2006.01)

(52) U.S. Cl. .................. 424/1.65; 424/1.81; 424/1.85; 424/1.89

(58) Field of Classification Search ............... 424/1.85, 424/1.81, 1.89, 1.11, 1.65, 1.69, 1.73, 1.41, 424/1.49, 1.53; 521/127
See application file for complete search history.

(56) References Cited

U.S. PATENT DOCUMENTS

| | | | |
|---|---|---|---|
| 4,826,672 A | 5/1989 | Milius et al. ................. 424/1.1 |
| 4,885,153 A | 12/1989 | Wilbur et al. ................. 424/1.1 |
| 5,565,185 A | 10/1996 | Hunter et al. ............... 424/1.85 |
| 5,569,447 A | 10/1996 | Lee et al. ................... 424/1.85 |
| 5,609,848 A | 3/1997 | Wilbur et al. ............... 424/1.85 |
| 5,720,935 A | 2/1998 | Kassis et al. ............... 424/1.73 |
| 5,746,997 A | 5/1998 | Reed ......................... 424/1.73 |
| 5,750,089 A | 5/1998 | Neumeyer et al. .......... 424/1.85 |
| 5,919,797 A | 7/1999 | Goodman et al. ........... 514/319 |
| 6,015,544 A | 1/2000 | Foged et al. ................ 424/1.85 |
| 6,019,957 A | 2/2000 | Miller et al. ................ 424/1.65 |

FOREIGN PATENT DOCUMENTS

| | | |
|---|---|---|
| WO | WO 98/18499 | 5/1998 |
| WO | WO 99/18053 | 4/1999 |

OTHER PUBLICATIONS

Culbert and Hunter; "Polymer Supported Radiopharmaceuticals: $^{123}$I and $^{131}$I-Labelled N-Isopropyl-4-Iodoamphetamine", Reactive Polymers 19: 247-253, (1993).

Djuric et al., "Silicon In Synthesis: Stabass Adducts—A New Primary Amine Protecting Group: Alkylation of Ethyl Glycinate," Tetrahedron Letters, 22: 1787-1790, (1981).

Gerigk et al., "Poolymer-Supported Organotin Hybrides as Immobilized Reagents for Free Radical Synthesis", No. 6: 448-452 (Jun. 1990).

Shapiro et al.; "Hypoglycemic Agents. III.$^{1-3}$ $N^1$-Alkyl- and Aralkylbiguanides", J. Am. Chem. Soc. 81:3728-3736.

Vaidyanathan and Zalutsky; "No-Carrier-added Synthesis of meta-[131 I] Iodobenzylguanidine", Appl. Radiat. Isot. 44(3): 621-628, (1993).

Wafelman et al.; "Synthesis, Radiolabelling and Stability of Radioiodinated m-Iodobenzylguanidine, a Review", Appl. Radiat. Isot 45(10):997-1007 (1994).

Form PCT/ISA/206, International Search Report for PCT/US 02/01958 mailed Sep. 25, 2002.

Culbert et al., "Polymer-supported radiopharmaceuticals: $^{123}$I- and $^{131}$I-labelled N-isopropyl-4-iodoamphetamine" Reactive Polymers, 19:247-253 (1993).

*Primary Examiner*—Michael Hartley
(74) *Attorney, Agent, or Firm*—Foley & Lardner LLP; Michel Morency; James F. Ewing

(57) ABSTRACT

One aspect of the present invention relates to novel compounds that can be used to prepare radiolabeled compounds in an effective manner. A second aspect of the present invention relates to a method of synthesizing radiolabeled compounds.

1 Claim, 7 Drawing Sheets insoluble polymeric precursor    soluble 3- or 4-radiobenzamide    insoluble polymeric sideproduct

POLYMER PRECURSORS OF RADIOLABELED COMPOUNDS, AND METHODS OF MAKING AND USING THE SAME

RELATED APPLICATION INFORMATION

This application claims the benefit of priority under 35 U.S.C. Section 119 to U.S. Provisional Patent Application No. 60/272,324, filed Mar. 2, 2001; and U.S. Provisional Patent Application No. 60/280,225, filed Mar. 30, 2001. These applications are hereby incorporated by reference in their entirety.

INTRODUCTION

Molecules labeled with radioactive isotopes have been used as both imaging agents in medical diagnosis as well as therapeutic agents in the treatment of cancer. Both radiolabeled small molecules and radiolabeled peptides and nucleotides have been used to diagnose tumors. In addition to their use as diagnostic tools, radiolabeled nucleosides have been used to treat tumors in mammals by injecting or infusing radiolabeled nucleosides directly to the affected site.

One common method of labeling molecules with radioactive isotopes for medical use is a stannylation process. While this process yields isotopically pure products, toxic tin by-products remain and must be separated before the radiolabeled molecules can be used. Furthermore, the unstable nature of radiolabeled molecules and their precursors lead to a short shelf life.

Radiolabeling of biosequences may also be achieved with activated esters. This method presents a similar problem of chemical purity and isotopic purity. While it is possible to attach a radioactive agent, for example, a benzamide, to a protein or peptide, only a small fraction of the resulting proteins or peptides actually bear a radioactive tag. The separation of radiolabeled material from non-radiolabeled material is particularly difficult since the protein or peptide is very large and the tag represents only a minor structural modification.

An improved method for radiolabeling molecules and biosequences is needed that overcomes some of the problems including toxic by-products, chemical purity and isotopic purity. Furthermore, there is a need for a precursor to radiolabeled molecules with a long shelf life.

SUMMARY OF THE INVENTION

In part this invention is directed to compounds that may be used to prepare radiolabeled compounds in an effective manner. This invention is also directed in part to methods of preparing radiolabeled compounds.

One aspect of the present invention relates to polymer precursor compounds represented by 1:

Poly—L—R—Y          1 wherein:

Poly represents a polymer;

L is selected from:

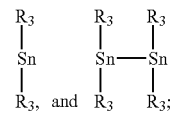

R represents aryl or heteroaryl;

Y represents hydrogen, alkyl, alkoxyl, carbonyl, formyl, amido, amino, alkylamino, dialkylamino, carboxamido, acylamino, (heterocyclcyl)acylamino, alkylcarboxyamido, $C(O)—R_4$, or $C(O)NH—R_4$;

$R_3$ represents independently for each occurrence alkyl, alkenyl or alkynyl;

$R_4$ represents hydrogen, alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside, or $—(CH_2)_m—R_{80}$;

$R_{80}$ represents independently for each occurrence aryl, cycloalkyl, cycloalkenyl, heterocyclyl, or polycyclyl; and m is an integer in the range 0 to 8 inclusive.

In one embodiment, L is $R_3—Sn—R_3$.

In another embodiment, Y is alkoxyl, formyl, amido, dialkylamino, carboxamido, alkoxyl, alkylcarboxyamido, $C(O)O—R_4$, $C(O)—R_4$ or $C(O)NH—R_4$. In another embodiment, Y is $C(O)O—R_4$, $C(O)—R_4$ or $C(O)NH—R_4$.

In one embodiment, $R_4$ is a peptide, protein, amino acid, antibody, nucleotide or nucleoside. In another embodiment, $R_4$ is a peptide or protein. In yet another embodiment, $R_4$ is a nucleotide or a nucleoside.

In one embodiment, $R_3$ is alkyl. In another embodiment, $R_3$ is butyl.

In one embodiment, the polymer is insoluble. In a further embodiment, the polymer is polystyrene, polyurethrane, poly(ethylene-co-vinyl acetate), polyethylene, polystyrene/rubber, or poly(ethylene-co-propylene). In another further embodiment, the polymer is polystyrene.

In another aspect, a method for preparing a radiolabeled compound is provided, wherein the method comprises reacting a polymer precursor compound, represented by structure 1, with an oxidant, a radiolabeled compound and optionally a buffer.

Another aspect of the present invention relates to methods of synthesizing radiolabeled compounds represented by formula 4:

X—R—Y          4 wherein

X is a radiolabeled molecule or atom;

R is aryl or heteroaryl;

Y is selected from hydrogen, alkyl, alkoxyl, carbonyl, formyl, amido, amino, alkylamino, dialkylamino, carboxamido, acylamino, (heterocyclcyl)acylamino, alkylcarboxyamido, $C(O)—R_4$, and $C(O)NH—R_4$;

$R_4$ represents hydrogen or optionally substituted alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside, or $—(CH_2)_m—R_{80}$;

$R_{80}$ represents independently for each occurrence aryl, cycloalkyl, cycloalkenyl, heterocyclyl, or polycyclyl; and m is an integer in the range 0 to 8 inclusive; the method comprising reacting a precursor compound 1 with a radiolabeled compound, an oxidant, and optionally a buffer to produce a compound of formula 4.

In a further embodiment, the radiolabeled compound is purified.

The methods of the present invention will find use in the synthesis of compounds useful for treatment of numerous ailments, conditions and diseases that afflict mammals, including but not limited to cancer. The methods of the present invention will find use in the synthesis of compounds for medical imaging including but not limited to imaging agents of breast cancer, sigma receptors, MAO receptors, and renal imaging.

An additional aspect of the present invention relates to the synthesis of combinatorial libraries of radiolabeled compounds using the methods of the present invention. In one embodiment, a method of synthesizing radiolabeled benzamides on a solid support is provided, which comprises: a) selecting a solid support comprising at least one compound attached to said solid support which compound comprises a benzoic acid moiety; b) reacting said moiety of said compound attached to said solid support with at least one amine to afford a benzamide bound to a solid support; and c) reacting said benzamide bound to said solid support with a radiolabeled compound or isotope, and an oxidant to yield a radiolabeled benzamides.

A further aspect of this invention contemplates a kit including subject compounds, and optionally instructions for their use. Uses for such kits include therapeutic and medical imaging applications. In one embodiment, a kit containing a radiolabeling system is provided, which comprises a polymer precursor compound and instructions for using said polymer precursor compound, wherein said polymer precursor compound comprises the polymer precursor compound shown in structure 1. In a further embodiment, the kit includes a filter or a filtration device. In another embodiment, the kit includes a chelating agent and optionally an auxiliary molecule.

These embodiments of the present invention, other embodiments, and their features and characteristics will be apparent from the description, drawings, and claims that follow.

DETAILED DESCRIPTION OF THE INVENTION

Figure 1:
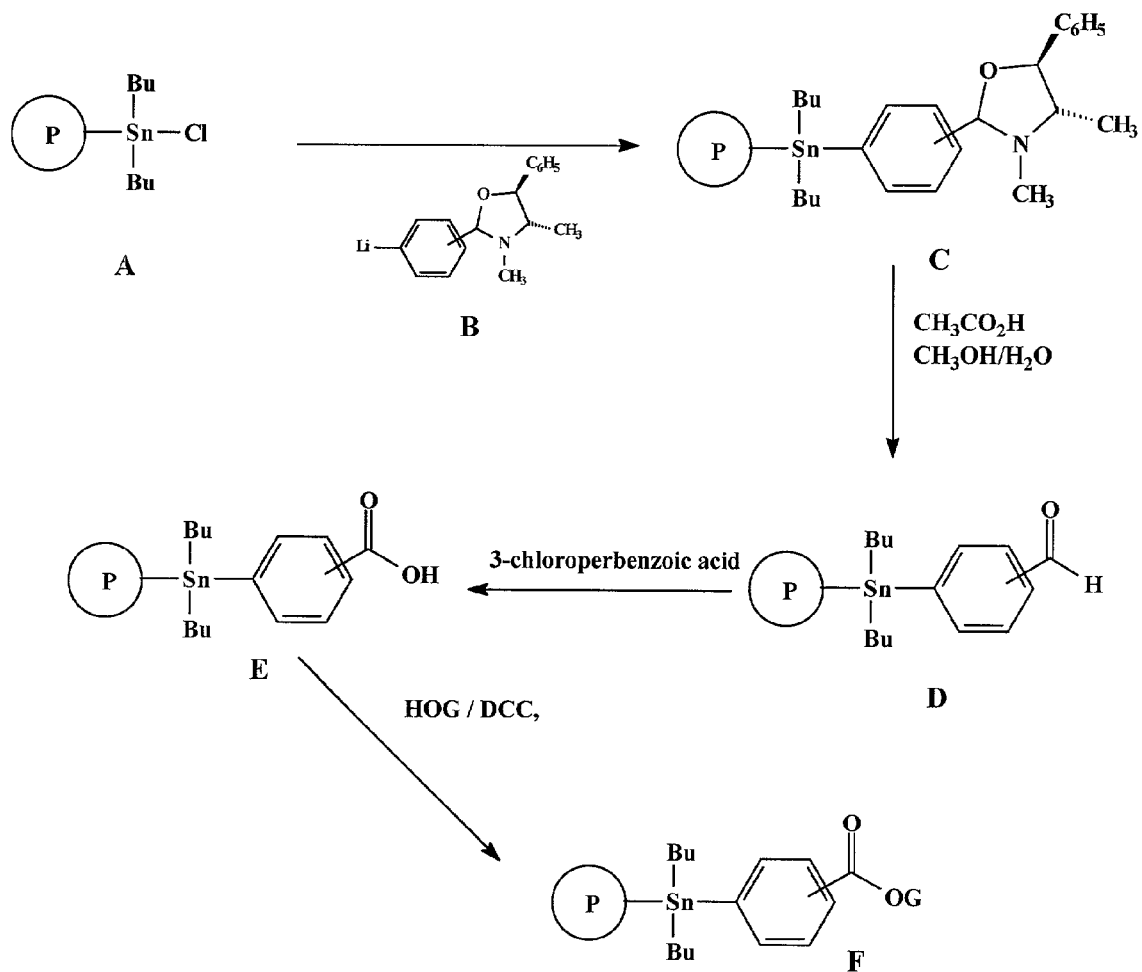
FIG. 1 depicts a route for the synthesis of certain compounds of the present invention.

Certain compounds of the present invention are precursors for the rapid and efficient radiolabeling of compounds. Since radiolabeled compounds may have a very short shelf life, a stable precursor may be needed for storage until use. Another aspect of the present invention relates to methods of synthesizing isotopically pure radiolabeled compounds without unwanted impurities.

In certain embodiments, the precursor compounds of the present invention are attached to a polymer as a trialkylarylstannane or trialkylaryldistannane, facilitating removal of the unwanted impurities by filtration of the polymer by-product. In one embodiment, the polymer may be insoluble.

The methods of synthesis of the present invention will find use in the synthesis of compounds useful for treatment of numerous ailments, conditions and diseases that afflict mammals, including cancer. The methods of synthesis of the present invention will also find use in medical and biological imaging. An additional aspect of the present invention relates to the synthesis of combinatorial libraries of precursors of radiolabeled compounds. A further aspect of this invention includes a kit including subject precursor compounds.

Definitions

The term "antibody" includes molecules consisting of polypeptide chains. It includes antibody fragments and antigen binding domain fragments, monoclonal antibodies, and immunoglobulins.

The terms "nucleotide" and "nucleoside" include nucleotides and nucleosides with base components of either purine or pyrimidine. Examples of nucleotides and nucleosides include adenosine, guanosine, cytidine, uridine, deoxyadenosine, deoxyguanosine, deoxycytidine, deoxythymidine, adenylate, guanylate, cytidylate, uridylate, deoxyadenylate, deoxyguanylate, deoxycytidylate, and thymidylate.

A polymer is any relatively high molecular weight molecule, the structure of which comprises the multiple repetition of units derived, actually or conceptually, from molecules of low relative molecular mass. A polymer which is part of a larger molecule is relatively inert to any reactivity of the other functional groups of the molecule. An insoluble polymer may be removed or separated by filtration.

The term "peptide" refers to an oligomer in which the monomers are amino acids (usually alpha-amino acids) joined together through amide bonds. Peptides are two or more amino acid monomers long, but more often are between 5 to 10 amino acid monomers long and may be even longer, i.e., up to 20 amino acids or more, and peptides longer than 20 amino acids are contemplated. Peptides include peptide hormones, peptide mimetics, conformationally restricted peptides, and peptide analogues.

The term "protein" is well known in the art and usually refers to a very large polypeptide, or set of associated homologous or heterologous polypeptides, that has some biological function. For purposes of the present invention the terms "polypeptide" and "protein" are largely interchangeable.

In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compound may include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

A "radiolabel" refers to molecule that is capable of generating a detectable image that may be detected either by the naked eye or using an appropriate techniques, e.g. positron emission tomography (PET), single photon emission tomography (SPECT) or magnetic resonance imaging (MRI). Certain exemplary labels are radionuclides, or radioactive isotopes of an element. Examples of radionuclides include $^{123}I$, $^{99m}Tc$, $^{18}F$, $^{68}Ga$, $^{62}Cu$, $^{111}In$, $^{131}I$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$, $^{11}C$, and $^{76}Br$. Additional labels are suitable for obtaining a magnetic resonance image (MRI), including unpaired spin atoms and free radicals (e.g. iron, lanthanides and gadolinium) and contrast agents (e.g. chelated DTPA manganese).

The term "solid support" includes insoluble, functionalized, polymeric materials to which library members or reagents may be attached, with or without a linker, allowing them to be readily separated, for example by filtration, centrifugation, from, for example, excess reagents, soluble reaction by-products, or solvents.

The term "heteroatom" as used herein means an atom of any element other than carbon or hydrogen. Exemplary heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In one embodiment, a straight chain or branched chain alkyl has 30 or fewer carbon atoms in its backbone (e.g., $C_1$–$C_{30}$ for straight chain, $C_3$–$C_{30}$ for branched chain), and in another embodiment, 20 or fewer. Likewise, exemplary cycloalkyls have from 3–10 carbon atoms in their ring structure, and in another embodiment, have 5, 6 or 7 carbons in the ring structure.

Unless the number of carbons is otherwise specified, "lower alkyl" as used herein means an alkyl group, as defined above, but having from one to ten carbons, and in one embodiment, from one to six carbon atoms in its backbone structure. Likewise, "lower alkenyl" and "lower alkynyl" have similar chain lengths. In one embodiment, alkyl groups are lower alkyls. In one embodiment, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

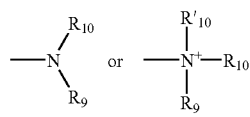

wherein R$_9$, R$_{10}$ and R'$_{10}$ each independently represent a group permitted by the rules of valence.

The term "acylamino" is art-recognized and refers to a moiety that can be represented by the general formula:

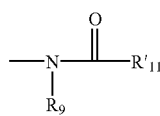

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

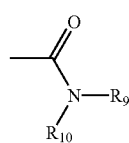

wherein R$_9$, R$_{10}$ are as defined above. In one embodiments, of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

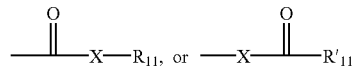

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

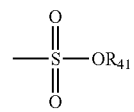

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

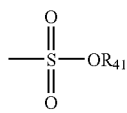

in which $R_{41}$ is as defined above.

The term "sulfonylamino" is art recognized and includes a moiety that can be represented by the general formula:

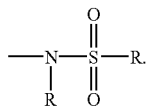

The term "sulfamoyl" is art-recognized and includes a moiety that can be represented by the general formula:

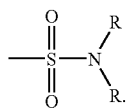

The term "sulfonyl", as used herein, refers to a moiety that can be represented by the general formula:

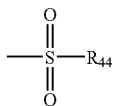

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

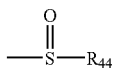

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as precursors), wherein one or more simple variations of substituents are made which do not adversely affect the efficacy of the compound to function as precursors of radiolabelled compounds. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

A "subject" shall mean a human or animal (e.g. a non-human mammal (e.g. rat, mouse, cat, dog, horse, sheep, cow, monkey), avian, or amphibian).

Compounds of the Invention

In certain embodiments, the compounds of the present invention are represented by the structure 1:

Poly—L—R—Y        1 wherein
Poly represents a polymer;
L is selected from:

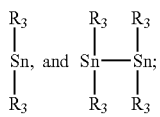

R represents aryl or heteroaryl;
Y is selected from hydrogen, alkyl, alkoxyl, carbonyl, formyl, amido, amino, alkylamino, dialkylamino, carboxamido, acylamino, (heterocyclcyl)acylamino, alkylcarboxyamido, C(O)-$R_4$, and C(O)NH—$R_4$;
$R_3$ represents independently for each occurrence hydrogen, alkyl, alkenyl or alkynl;
$R_4$ represents hydrogen, alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside, or —$(CH_2)_m$—$R_{80}$;
$R_{80}$ represents independently for each occurrence aryl, cycloalkyl, cycloalkenyl, heterocyclyl, or polycyclyl; and
m is an integer in the range 0 to 8 inclusive.

In certain embodiments, the compounds of the present invention are represented by structure 1 and the attendant definitions, wherein $R_3$ is $C_4H_9$.

In certain embodiments, the compounds of the present invention are represented by structure 1 and the attendant definitions, wherein R is selected from the structures:

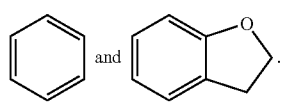

In certain embodiments, the compounds of the present invention are represented by structure 1 and the attendant definitions, wherein Y and Poly—Sn($R_3$)$_2$ are bonded to the same ring of R; and there is meta or para relationship between Y and Poly—Sn($R_3$)$_2$ In certain embodiments, the polymer of structure 1 is functionalized by the moiety L on at least one monomeric unit of the polymer. In another embodiment, the polymer of structure 1 is functionalized by the moiety L on substantially all monomeric units of the polymer.

In certain embodiments, the compounds of the present invention are represented by structure 1 and the attendant definitions, wherein Y comprises an amino group at the terminus of a peptide which serves to bind the peptide.

In certain embodiments, the compounds of the present invention are represented by structure 1 and the attendant definitions, wherein Y comprises an amino group within a peptide which serves to bind the peptide.

In certain embodiments, the compounds of the present invention are represented by structure 1, wherein Y is C(O)NH-peptide.

In certain embodiments, the compounds of the present invention are represented by structure 1 and the attendant definitions, wherein Y includes an amino group within an antibody.

In certain embodiments, a compound of the invention is represented by the structure A:

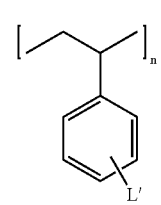

wherein L' is independently for each occurrence H or —$CH_2$—L—R—Y;
at least one instance of L' is not H;
L is selected from:

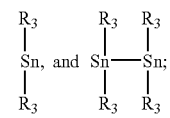

R represents aryl or heteroaryl;
Y is selected from hydrogen, alkyl, alkoxyl, carbonyl, formyl, amido, amino, alkylamino, dialkylamino, carboxamido, acylamino, (heterocyclcyl)acylamino, alkylcarboxyamido, C(O)—$R_4$, and C(O)NH—$R_4$;
$R_3$ represents independently for each occurrence alkyl, alkenyl or alkynl;
$R_4$ represents hydrogen, alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside, or —$(CH_2)_m$—$R_{80}$;
$R_{80}$ represents independently for each occurrence aryl, cycloalkyl, cycloalkenyl, heterocyclyl, or polycyclyl;
m is an integer in the range 0 to 8 inclusive; and
n is an integer from 1 to about 1000.

In certain embodiments, compounds of the present invention are represented by structure 2:

$$\text{Poly} - \underset{\underset{R_3}{|}}{\overset{\overset{R_3}{|}}{Sn}} - R - Y \qquad (2)$$

wherein

Poly represents a polymer;

R represents aryl;

Y is selected from hydrogen, alkyl, alkoxyl, carbonyl, formyl, amido, amino, alkylamino, dialkylamino, carboxamido, acylamino, (heterocyclcyl)acylamino, alkylcarboxyamido, $C(O)-R_4$, and $C(O)NH-R_4$;

$R_3$ is represents independently for each occurrence alkyl, and alkenyl;

$R_4$ represents hydrogen, alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside, or $-(CH_2)_m-R_{80}$;

$R_{80}$ represents independently for each occurrence aryl, cycloalkyl, cycloalkenyl, heterocyclyl, or polycyclyl; and m is an integer in the range 0 to 8 inclusive.

In certain embodiments, the compounds of the present invention are represented by structure 2 and the attendant definitions, wherein $R_3$ is $C_4H_9$.

In certain embodiments, the compounds of the present invention are represented by structure 2 and the attendant definitions, wherein R is selected from the structures:

and

In certain embodiments, the compounds of the present invention are represented by structure 2 and the attendant definitions, wherein Y and Poly—$Sn(R_3)_2$ are bonded to the same ring of R; and there is meta or para relationship between Y and Poly—$Sn(R_3)_2$ In certain embodiments, the polymer of structure 2 is functionalized by the moiety L on at least one monomeric unit. In another embodiment, the polymer of structure 2 is functionalized by the moiety L on substantially all monomeric units.

In certain embodiments, the compounds of the present invention are represented by structure 2 and the attendant definitions, wherein Y comprises an amino group at the terminus of a peptide which serves to bind the peptide.

In certain embodiments, the compounds of the present invention are represented by structure 2 and the attendant definitions, wherein Y comprises an amino group within a peptide, which serves to bind the peptide.

In certain embodiments, the compounds of the present invention are represented by a structure 2, wherein Y is C(O)NH-peptide.

In certain embodiments, the compounds of the present invention are represented by structure 2 and the attendant definitions, wherein Y comprises an amino group within an antibody.

In certain embodiments, a compound of the invention are represented by structure B:

(B)

wherein L' is independently for each occurrence H or $-CH_2-L-R-Y$;

at least one instance of L' is not H;

L is:

$$\underset{\underset{R_3}{|}}{\overset{\overset{R_3}{|}}{Sn}};$$

R represents aryl;

Y is selected from hydrogen, alkyl, alkoxyl, carbonyl, formyl, amido, amino, alkylamino, dialkylamino, carboxamido, acylamino, (heterocyclcyl)acylamino, alkylcarboxyamido, $C(O)-R_4$, and $C(O)NH-R_4$;

$R_3$ represents independently for each occurrence alkyl, alkenyl or alkynl;

$R_4$ represents hydrogen, alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside, or $-(CH_2)_m-R_{80}$;

$R_{80}$ represents independently for each occurrence aryl, cycloalkyl, cycloalkenyl, heterocyclyl, or polycyclyl;

m is an integer in the range 0 to 8 inclusive; and n is an integer from 1 to about 1000.

In certain embodiments, a compound of the present invention is represented by the structure 3:

$$\text{Poly} - \underset{\underset{R_3}{|}}{\overset{\overset{R_3}{|}}{Sn}} - R - Y \qquad (3)$$

wherein

Poly represents a polymer;

R represents aryl;

Y is $C(O)N-R_4$ and $C(O)-R_4$;

$R_3$ is represents independently for each occurrence an alkyl, or alkenyl;

$R_4$ represents hydrogen or optionally substituted alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside, or $-(CH_2)_m-R_{80}$;

$R_{80}$ represents independently for each occurrence aryl, cycloalkyl, cycloalkenyl, heterocyclyl, or polycyclyl; and m is an integer in the range 0 to 8 inclusive.

In certain embodiments, the compounds of the present invention are represented by structure 3 and the attendant definitions, wherein $R_3$ is $C_4H_9$.

In certain embodiments, the compounds of the present invention are represented by structure 3 and the attendant definitions, wherein R is selected from the structures:

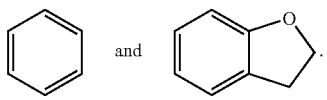

In certain embodiments, the compounds of the present invention are represented by structure 3 and the attendant definitions, wherein Y and Poly—Sn($R_3$)$_2$ are bonded to the same ring of R; and there is meta or para relationship between Y and Poly—Sn($R_3$)$_2$.

In certain embodiments, the polymer of structure 3 is functionalized by the moiety L on at least one monomeric unit. In another embodiment, the polymer of structure 3 is functionalized by the moiety L on substantially all monomeric units.

In certain embodiments, the compounds of the present invention are represented by structure 3 and the attendant definitions, wherein Y includes an amino group at the terminus of a peptide which serves to bind the peptide.

In certain embodiments, the compounds of the present invention are represented by structure 3 and the attendant definitions, wherein Y includes an amino group within a peptide, which serves to bind the peptide.

In certain embodiments, the compounds of the present invention are represented by a structure 3 where Y is C(O)NH-peptide.

In certain embodiments, the compounds of the present invention are represented by structure 3 and the attendant definitions, wherein Y includes an amino group within an antibody.

The polymer of structures 1, 2, and 3 may be any known polymer. Suitable polymers include polyethylene glycols, polystyrenes, polyamides, peptides, and the like. Exemplary polymers include polystyrene, polyurethrane, poly(ethylene-co-vinyl acetate), polyethylene, polystyrene/rubber, and poly(ethylene-co-propylene). In one embodiment, the polymer of structures 1, 2, and 3 is polystyrene.

Methods of the Invention

Another aspect of the present invention relates to methods of synthesizing radiolabelled compounds of the formula 4:

X—R—Y      4 wherein
X is a radioactive isotope of an element;
R is aryl or heteroaryl;
Y is selected from hydrogen, alkyl, alkoxyl, carbonyl, formyl, amido, amino, alkylamino, dialkylamino, carboxamido, acylamino, (heterocyclcyl)acylamino, alkylcarboxyamido, C(O)—$R_4$, and C(O)NH—$R_4$.
$R_4$ represents hydrogen or optionally substituted alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside or —(CH$_2$)$_m$—$R_{80}$;
$R_{80}$ represents independently for each occurrence aryl, cycloalkyl, cycloalkenyl, heterocyclyl, or polycyclyl;
m is an integer in the range 0 to 8 inclusive; the method comprising reacting a precursor compound 1, 2, or 3 with a radiolabeled compound or radioisotope, an oxidant, and optionally a buffer to produce a compound of formula 4.

In general, the radiolabeled compounds 4 may be obtained from compounds 1, 2 and 3 in high yield, through site-specific destannylation chemistry. In an embodiment, the oxidant and the optional buffer are selected from chloramine-T in ethanol/water with or without acetic acid; N-chlorosuccinimide with acetic acid in methanol; tert-butylhydroperoxide with acetic acid in chloroform; Iodogen with a phosphate buffer; and iodobeads with or without acetic acid in methanol.

In a further embodiment, a radiohalogenated compound 4 may be obtained by the reaction:

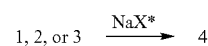

where *X is a radioisotope of a halogen. In another embodiment, compounds 1, 2, or 3 may be treated with any alkali earth metal-radiohalogen compound to yield compound 4.

Another aspect of the present invention relates to methods of synthesizing radiolabelled compounds of the formula 5:

X—R—Y      5 wherein
X is a radioactive isotope of an element;
R is aryl;
Y is selected from C(O)N—$R_4$, and C(O)—$R_4$;
$R_4$ represents hydrogen or optionally substituted alkyl, alkenyl, heteroalkyl, cycloalkyl, heterocycloalkyl, aryl, heteroaryl, aralkyl, heteroaralkyl, peptide, protein, amino acid, antibody, nucleotide, nucleoside or —(CH$_2$)$_m$—$R_{80}$;
$R_{80}$ represents independently for each occurrence aryl, cycloalkyl, cycloalkenyl, heterocyclyl, or polycyclyl,
m is an integer in the range 0 to 8 inclusive; and the method comprising reacting a precursor compound 1, 2, or 3 with a radiolabeled compound, an oxidant, and optionally a buffer, to produce a compound of formula 5.

In general, the radiolabeled compounds 5 may be obtained from compounds 1, 2 and 3 in high yield, through site-specific destannylation chemistry. In an embodiment, the oxidant and the optional buffer are selected from chloramine-T in ethanol/water with or without acetic acid; N-chlorosuccinimide with acetic acid in methanol; tert-butylhydroperoxide with acetic acid in chloroform; Iodogen with a phosphate buffer; and iodobeads with or without acetic acid in methanol.

In an embodiment, a radiohalogenated compound 5 may be obtained by the reaction:

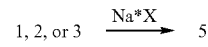

In a particular embodiment, X is selected from the radioisotopes $^{18}$F, $^{11}$C, $^{76}$Br, $^{123}$I, $^{131}$I and $^{125}$I.

The radiolabeled compounds may be free of toxic components associated with, for example, the precursor to the radiolabeled compound, e.g., compounds 1, 2 or 3. The synthetic approach in this invention maintains the advantages of rapid and clean reaction, but also offers a solution to the purification problem. Treatment of the insoluble polymeric precursor compounds of the instant invention, with a radioisotope and an oxidant, releases radiolabeled compounds into solution while any excess precursor and the insoluble polymeric side-product may be removed by filtration. Thus simple and rapid filtration may result in chemically pure material.

In another embodiment, the polymer-supported radiopharmaceutical precursors in the instant invention have chemical stabilities unusually greater than their non-supported counterparts without any particular precautions being taken, with greater shelf life.

In another embodiment, radiopharmaceutical compounds formed by this process are produced at the no-carrier-added level and will have a specific activity as high as the source of radioisotope. This approach produces the high specific activity radiopharmaceutical compound required for receptor specificity within the body.

In the another embodiment, a radiolabeled peptide or protein formed by this method will be isotopically pure.

In the another embodiment, a radiolabeled antibody formed by this method will be isotopically pure.

In the another embodiment, a radiolabeled nucleotide or nucleoside formed by this method will be isotopically pure.

The methods of the present invention will find use in the synthesis of compounds useful for treatment of numerous ailments, conditions and diseases that afflict mammals, including but not limited to cancer. The methods of the present invention will find use in the synthesis of the compounds for medical imaging including but not limited to imaging agents of breast cancer, sigma receptors, MAO receptors, and renal imaging.

One aspect of the present invention relates to method for synthesizing each of the compounds 1, 2, 3, 4, and 5. In one embodiment, the method comprises a polymer bound arylstannane covalently bound to an aldehyde treated with a oxidizing agent to convert the aldehyde to a carboxylic acid. In a further embodiment, the method comprises a polymer bound arylstannane covalently bound to a carboxylic acid treated with an acid to convert to a polymer bound arylstannane covalently bound to an amide. In an alternate embodiment, the method comprises a polymer bound arylstannane covalently bound to a carboxylic acid, and then converted to an activated ester intermediate. The activated ester intermediate may then be reacted with an amine to yield a polymer bound arylstannane covalently bound to an amide. These amides may then be treated with a radiolabeled compound and an oxidant to yield a radiolabeled compound.

In one particular embodiment, the invention relates to the synthesis of polymer-supported benzoic acids and activated esters of benzoic acid (See FIG. 1). The synthetic route commences with the insoluble polymer-supported chlorostannane A that is treated with an excess of the organolithium reagent B. This produces the insoluble polymer C that in turn is converted by mild acid hydrolysis into the insoluble polymer-supported benzaldehydes D. The benzaldehydes D are then converted into the corresponding polymer-supported meta- and para-benzoic acids E by treatment with an excess of the oxidizing agent 3-chloroperbenzoic acid. In turn, the meta- and para-benzoic acids E are used directly or are converted to activated esters F through use of a selected hydroxyl compound (HOG=N-hydroxysuccinimide, pentafluorophenol or tetrafluorophenol) and coupling agent such as DCC (dicyclohexylcarbodiimide) under standard coupling conditions.

After each step the desired insoluble polymeric materials are washed several times with appropriate solvents to remove any excess reagents and unwanted by-products. In each case the polymers have been characterized by spectroscopy ($^{119}$Sn MAS NMR and IR (DRIFT)) and by analyzing the products of iodinolysis.

Figure 2:
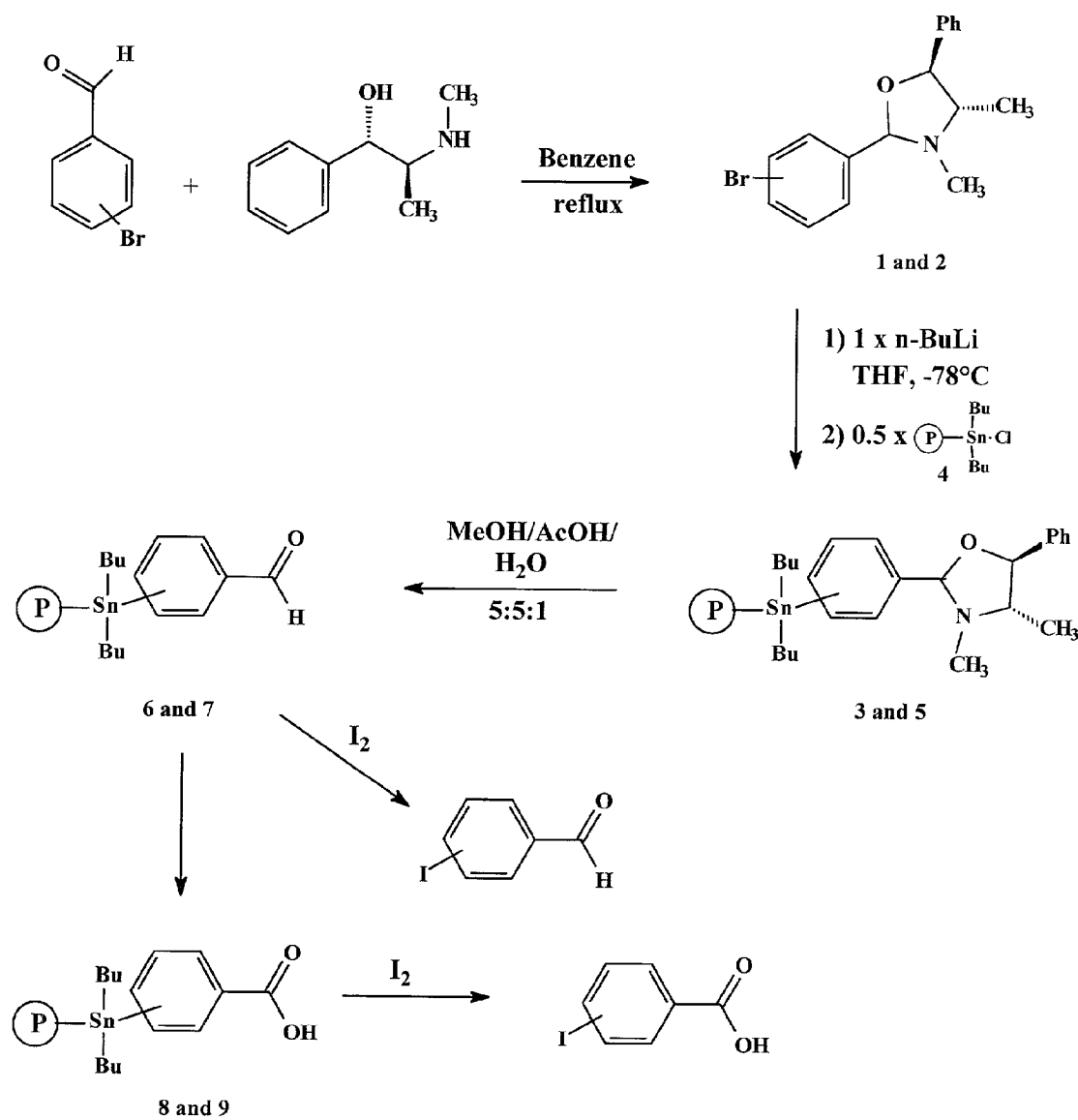
FIG. 2 depicts a route for the synthesis of certain compounds of the present invention (See Examples 1–8).

In another particular embodiment, the invention relates to the synthesis of polymer-supported benzoic acid (See FIG. 2). This route was followed to the polymer-bound benzoic acid from either the 3-bromo or 4-bromobenzaldehyde which were first converted to the corresponding oxazolidines (1 and 2, FIG. 2). The protecting agent (pseudoephedrin) was chosen because the derived oxazolidine is stable to n-butyllithium and may be removed under mildly acidic conditions. Using a Dean-Stark trap to remove water, the protection reaction proceeded in a clean manner to give the desired oxazolidines in high yield, 94% and 98% (of 1 and 2, FIG. 2) from the 3 and 4-bromobenzaldehydes, respectively.

The second step entails the attachment of the oxazolidine-protected benzaldehydes to the stannane polymer, via formation of an aryl-lithium intermediate and its subsequent reaction with the chlorostannane polymer 4 (FIG. 2). The organolithium was formed at −78° C. using one equivalent of n-butyllithium to which the chlorostannane polymer was added using the organolithium in two-fold excess. The reaction mixture was allowed to warm to room temperature overnight. The reaction mixture was then quenched with methanol and the insoluble polymeric material was washed with combinations of methanol, water and acetone. In certain cases the filtrates were retained to allow determination of the extent of conversion to organolithium and attachment to the polymer.

The insoluble polymeric materials were analyzed in three ways: solid phase MAS $^{119}$Sn NMR spectroscopy and IR using a DRIFT attachment as well as by iodinolysis of the polymer. The products of the latter reaction, monitored by HPLC, allow for determination of the type and quantification of the amount of aromatic compounds attached to the polymer.

The solid phase MAS $^{119}$Sn NMR spectrum of the polymer-bound 3-protected aldehyde (3) showed the presence of one peak at −42.1 ppm and the absence of a peak at 149.6 ppm. A peak at −42.1 ppm is consistent with the presence of a tin atom of the type found in trialkylarylstannanes while a peak at 149.6 would indicate unreacted chlorostannane polymer. This data indicates that all the sites on the polymer have reacted and are occupied by aryl groups.

The solid phase IR spectrum of the polymer-bound 4-protected aldehyde (5) showed the presence of a C-O stretch around 1050 cm$^{-1}$ consistent with the presence of the oxazolidine ring. Iodinolysis proved to be an unreliable method of analysis since it is thought that the oxazolidine ring is susceptible to the reaction conditions.

Removal of the protecting group was achieved by treatment of the polymers with an acetic acid solution at room temperature for about 24 h. The insoluble polymeric material recovered from this treatment was washed with combinations of methanol, water and acetone. Analysis of the material (from the reaction of the polymer-bound 3-protected aldehyde (3 FIG. 2) by MAS $^{119}$Sn NMR spectroscopy showed a single peak at −39.0 ppm. This change in shift, although small, was seen consistently. The solid phase IR spectrum of the polymer (from the reaction of the polymer-bound 4-protected aldehyde (5, FIG. 2) showed a peak at 1707 cm$^{-1}$ indicative of the presence of a carbonyl group. The peak at 1050 cm$^{-1}$ attributed to the oxazolidine disappeared. In addition, a peak at 2715 cm$^{-1}$ is indicative of the presence of an aldehyde. HPLC analysis of the filtrates after iodinolysis indicated the presence of about 0.74 and about 0.78 mmol per gram of polymer of 3-iodobenzaldehyde and 4-iodobenzaldehyde, respectively. The values for the attachment ranged from about 0.40–0.99 mmol per gram of polymer, with the majority between about 0.7–0.9 mmol per gram.

With the aldehydes, the conversion reaction to acids was forwarded. The tin carbon bond is susceptible to cleavage by acid, so an oxidizing agent that may be able to carry out this conversion under mildly acid conditions was chosen such that the oxidation was carried out by treatment of the polymer-bound aldehydes with a mCPBA solution at room temperature overnight. The insoluble polymeric materials recovered form these treatments were washed with a combination of NaOH, HCl, methanol, water and acetone. Analysis of the material (from the reaction of the polymer-bound 3-aldehyde 6) by MAS $^{119}$Sn NMR spectroscopy showed a peak at −39.3 ppm. The solid phase IR spectrum (from the reaction of the polymer-bound 4-aldehyde 7) showed a peak at 1695 cm$^{-1}$ indicative of the presence of a carbonyl group. The shift in the carbonyl peak position is consistent with conversion of an aldehyde to a carboxylic acid. Analysis of the filtrate of the iodinolysis reactions by HPLC showed the presence of 0.33 and 0.66 mmol per gram of polymer of 3-iodobenzoic acid and 4-iodobenzoic acid, respectively. The lowering in the loading of the benzoic acid polymers indicates that protodestannylation may have occurred even under these mildly acidic conditions.

Figure 3:
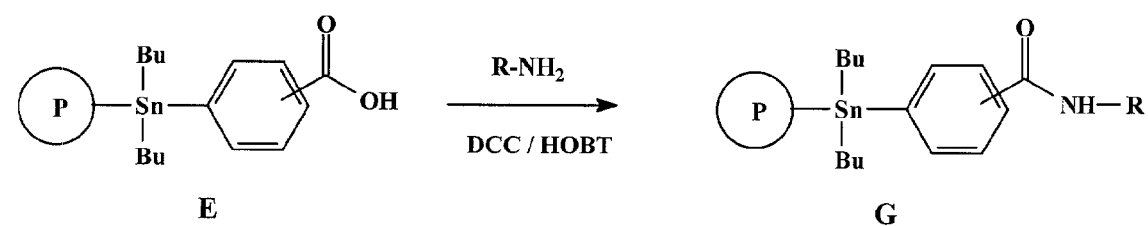
FIG. 3 depicts a route for the synthesis of certain compounds of the present invention.

In another embodiment the invention relates to the synthesis of polymer supported amides (FIG. 3). For molecules bearing an amino group (primary or secondary), it is possible to form a polymer-supported amide by direct reaction of the polymer-supported benzoic acids E, with the appropriate amine (R—NH$_2$) and coupling reagents such as DCC (dicyclohexylcarbodiimide) and HOBT (1-hydroxybenzotriazole)

Figure 4:
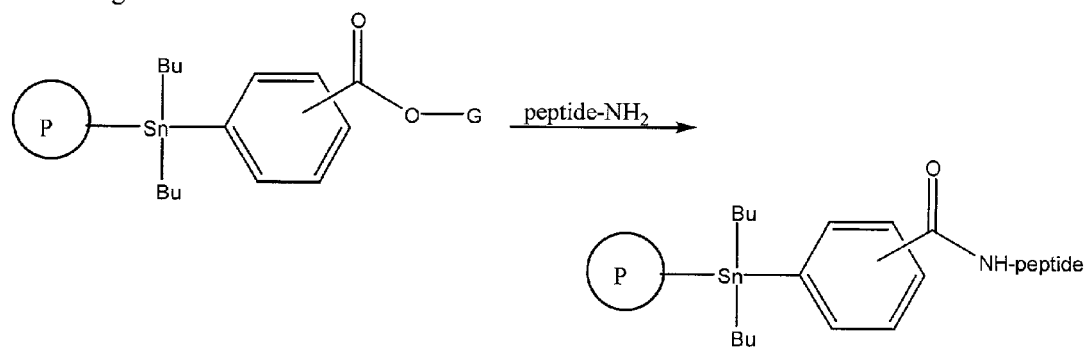
FIG. 4 depicts a route for the synthesis of certain compounds of the present invention.
Figure 4:
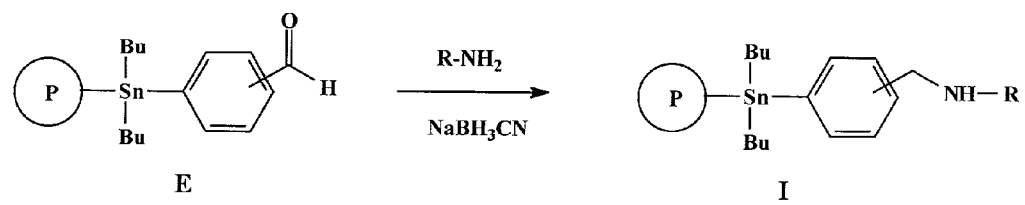

In another embodiment, the invention relates to the synthesis of polymer supported benzamide and benzylamine precursors (See FIG. 4). A synthetic route to benzamides is through the intermediacy of an activated ester (F). An amino group (end terminus or internal lysines) binds the peptide to the polymer. Polymer-supported benzaldehydes D are the precursors to the polymer-supported benzoic acids E as well as polymer-supported benzylamines I. Benzylamines I are precursors for radioiodinated pharmaceuticals bearing the benzylamine functionality. The amine (RNH$_2$) may be selected from a wide range of primary and secondary amines.

Figure 5:
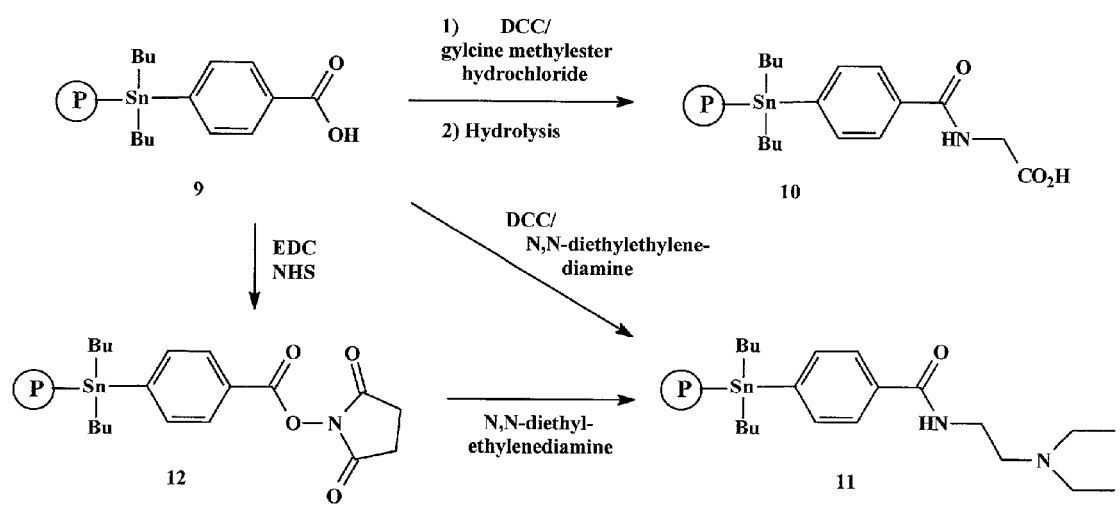
FIG. 5 depicts a route for the synthesis of certain compounds of the present invention (See Examples 9–12).

In another embodiment, the invention relates to the synthesis of polymer supported benzamides (See FIG. 5). The formation of benzamides may be carried out in two ways: directly from the acid, with coupling reagents like DCC, or by the formation of an active ester (e.g., NHS ester), that may be reacted with the appropriate amine to give a benzamide. The latter method is applicable to amines, amino acids and proteins, whereas the direct method is restricted to amines.

Two direct and one indirect coupling reactions were carried out with the polymer-bound 4-benzoic acid 9. The polymer 9 was treated with a solution of DCC and the hydrochloride salt of methyl glycerate. The suspension was stirred at room temperature for 5 days, and the insoluble polymeric material was washed with combinations of methanol, acetone and dichloromethane. Hydrolysis of the methyl ester was accomplished by treating the polymeric material with a solution of NaOH under refluxing conditions for 4 hrs. The polymeric material was washed with combinations of methanol, water, HCl and acetone. Analysis of the filtrate of the iodinolysis reaction by HPLC revealed 0.58 mmol of 4-iodohippuric acid per gram of polymer of 10. This indicates that the coupling reaction has gone to completion.

Treatment of 9 with a solution of DCC and N, N-diethylethylenediamine at room temperature for 7 days gave the benzamide bound polymer 11 after washing the polymeric material with combinations of methanol, acetone and dichloromethane. HPLC analysis of the filtrate of the iodinolysis reaction revealed 0.35 and 0.08 mmol of the benzamide and the acid, respectively indicating that the reaction had not gone to completion under the conditions employed.

To investigate indirect amide formation through an activated ester of polymer 9 the preparation of polymer-bound benzamide 11 was attempted. Polymer 9 was treated with a solution containing EDC and NHS at room temperature for 70 hrs. The insoluble material was washed with combinations of methylene chloride, to give the polymer-bound active ester 12. Alternatively, pentafluorophenyl and tetrafluorophenyl esters may be made. The IR spectrum of this polymer showed two peaks at 1773 and 1743 cm$^{-1}$ indicative of the presence of appropriate carbonyl groups. Polymer 12 was then treated with a solution of N,N-diethylethylenediamine at room temperature for 23 hrs. The insoluble polymeric compound was washed with a combination of methanol, water and acetone. HPLC analysis of the filtrate of the iodinolysis reaction revealed 0.43 and 0.09 mmol of benzamide and acid, respectively indicating incomplete conversion under these conditions. Polymer-supported benzoic acids were therefore joined through either the 3- (8) or 4- (9) positions on the aromatic ring. The 4-substituted benzoic acid (9) has been successfully converted to polymer-bound benzamides either directly or indirectly through an N-hydroxysuccinimidyl ester.

Figure 6:
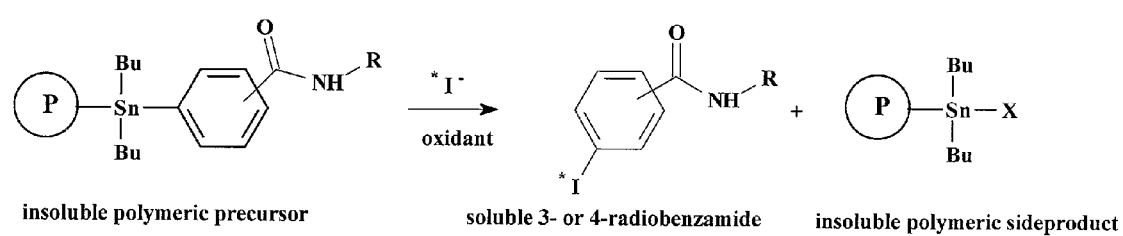
FIG. 6 depicts a route for the synthesis of certain compounds of the present invention.

In another embodiment, the invention relates to the synthesis of radiolabeled compounds (see FIG. 6). The insoluble polymeric precursor is treated with radioiodine and an oxidant, and releases 3- or 4-radioiodobenzamide into solution. Excess precursor and the insoluble polymeric side product, containing the stannane portion are removed by filtration. In a further embodiment, purification of benzamides from iodinolysis is undertaken.

Combinatorial Libraries

The subject methods and compounds readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library may be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules.

See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with sequenceable bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In some embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Kits

The invention provides for a kit in which precursor compounds of the present invention are used according to a method described herein to provide a desired radiolabeled compound for imaging or therapy. A kit comprises one or more of the compounds described above, in combination with a pharmaceutically acceptable carrier such as sterile normal saline or human serum albumin. Other substances may also be used as carriers in accordance with this embodiment of the invention, for example, detergents, dilute alcohols, carbohydrates, auxiliary molecules, and the like. A kit of the invention may of course also contain such other items as may facilitate its use, such as syringes, instructions, buffers, reducing agents, buffers, reducing agents, reaction vials, and the like.

In one embodiment, a kit includes an oxidant or an oxidizing agent, and about 1 to about 30 mCi of the radionuclide-labeled imaging agent described above, in combination with a pharmaceutically acceptable carrier, for diagnostic or imaging use. In another embodiment, a kit includes an oxidant or an oxidizing agent, and about 10 to about 5000 mCi of the radionuclide-labeled imaging agent described above, in combination with a pharmaceutically acceptable carrier, for therapeutic use. The compounds of the present invention and the carrier may be provided in solution or in lyophilized form. When the compounds of the present invention and carrier of a kit are in lyophilized form, the kit may optionally contain a sterile and physiologically acceptable reconstitution medium such as water, saline, buffered saline, and the like.

In another embodiment, a kit of the invention includes a filter or filtration device to remove excess precursor compound or the insoluble polymeric side product.

In another embodiment, a kit of the invention may produce or contain precursor compounds of the present invention which has been covalently or non-covalently combined with a chelating agent; an auxiliary molecule such as mannitol, gluconate, glucoheptonate, tartrate, and the like; and a reducing agent such as $SnCl_2$, Na dithionite or tin tartrate. The precursor compound/chelating agent and the auxiliary molecule may be present as separate components of the kit or they may be combined into one kit component. The unlabeled precursor compound/chelating agent, the auxiliary molecule, and the reducing agent may be provided in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

(4S, 5S)-2-(3-bromophenyl)-3,4-dimethyl-5-phenyl-1,3-oxazolidine (7)

Into a one necked 250 mL round-bottom flask, equipped with a Dean-Stark trap and a condenser was placed 8.78 g (47.5 mmol) of 3-bromobenzaldehyde and 7.83 g (47.4 mmol), of (S, S)-(+)-pseudoephedrine followed by 180 mL of benzene. After reflux for 18 hrs, the benzene was removed using a rotary-evaporator, to give a yellow oil, which solidified upon standing. A white solid (mp. 73–75° C.) was obtained after recrystallization from hexanes, 14.78 g (94%).

$^1$H NMR ($CDCl_3$) ppm: 7.75 (s, 1H), 7.51–7.26 (m, 8H), 4.93 (s, 1H), 4.76 (d, 1H), 2.56 (m, 1H), 2.23 (s, 3H), 1.23 (d, 3H). $^{13}$C NMR ppm: 141.96, 139.91, 132.08, 130.95, 129.86, 128.37, 128.00, 126.76, 126.61, 122.50, 98.60, 86.60, 68.62, 35.12, 14.23.

EXAMPLE 2

(4S, 5S)-2-(4-bromophenyl)-3,4-dimethyl-5-phenyl-1,3-oxazolidine (8)

In an analogous manner, 500 mg (2.7 mmol) of 4-bromobenzaldehyde, 450 mg (2.7 mmol), of (S, S)-(+)-pseudoephedrine and 40 mL of benzene were refluxed for 18 hrs. Solvent evaporation yielded a viscous yellow oil, 883 mg (98%).

$^1$H NMR ($CDCl_3$): 7.42 (d, 2H), 7.35–7.20 (m, 7H), 4.82 (s, 1H), 4.65 (d, 1H), 2.45 (m, 1H), 2.09 (s, 3H), 1.12 (d, 3H). $^{13}$C NMR: 139.97, 138.53, 131.38, 129.68, 128.33, 127.94, 126.56, 122.91, 98.69, 86.50, 68.59, 35.00, 14.19.

EXAMPLE 3

Poly-(4S, 5S)-2-(3-{dibutyl[2-(3-and 4-vinylphenyl)ethyl]stannyl}phenyl)-3, 4-dimethyl-5-phenyl-1,3-oxazolidine)-co-divinylbenzene (9)

The protected 3-bromobenzaldehyde 7, (2.90 g, 8.7 mmol), was added into a three-necked 200 mL round-bottom flask, equipped with a T-bore stopcock, a rubber septum and a powder addition side arm containing 4.01 g of chlorostannane polymer 10 (~5.9 mmol of SnCl). Under a flow of argon, 80 mL of freshly distilled dry THF was added by syringe. The flask and its contents were outgased three times at dry ice/acetone temperatures and an argon atmosphere was introduced. To the solution of 7 in THF at −78° C., n-butyllithium (3.0 mL, 7.5 mmol, 2.5 M) was added dropwise with the resultant formation of a yellow color. After 2 h at −78° C., the polymer was tipped into the THF solution, and the suspension was allowed to stir for 18 h and warm slowly to RT. To the suspension about 3 mL of methanol was added and the suspension was filtered. The solid was washed with methanol, water, methanol/water/acetone, methanol/acetone and methanol several times to yield 4.3 g of 9.

$^{119}$Sn MAS NMR: −42.1 ppm.

EXAMPLE 4

Poly-(4S, 5S)-2-(4-{dibutyl[2-(3-and 4-vinylphenyl)ethyl]stannyl}phenyl)-3, 4-dimethyl-5-phenyl-1,3-oxazolidine)-co-divinylbenzene (11)

1.02 g (3.1 mmol) of the protected 4-bromobenzaldehyde 8, in 35 mL of THF, was reacted with 1.2 mL (3.0 mmol, 2.5 M) of n-butyllithium for 2 h at −78° C. Polymer 10, 1.05 g (~1.6 mmol of SnCl) was tipped into the THF solution, and the suspension was allowed to stir for 17 hrs. After addition of ~2 ml of methanol, the suspension was filtered and washed in the same manner as 9 to afford 1.24 g of 11.

IR (DRIFT, solid): ~1050 $cm^{-1}$ C-O stretch.

EXAMPLE 5

Poly-(3-{dibutyl[2-(3-and-4-vinylphenyl)ethyl] stannyl}benzaldehyde)-co-divinylbenzene (12)

The protected aryl-bound polymer 9 (3.98 g) was treated with a mixture of 25 mL of methanol, 9 mL of water and 25 mL of acetic acid by gentle shaking for 27 h. The solid was recovered by filtration and was washed successively with methanol, water, methanol/water/acetone, methanol/acetone, and methanol to yield 3.65 g of the aldehyde-bound polymer 12.

Iodinolysis: 0.74 mmol of 3-iodobenzaldehyde per gram of polymer.
$^{119}$Sn MAS NMR: −39.0 ppm.

EXAMPLE 6

Poly-(4-{dibutyl[2-(3-and 4-vinylphenyl)ethyl] stannyl}benzaldehyde)-co-divinylbenzene (13)

1.22 g of the protected aryl-bound polymer 11, was treated with a mixture of 5 mL of methanol, 1.5 mL of water and 5 mL of acetic acid by shaking for 17 hrs. The solid was filtered and washed as before to yield 1.00 g of 13.

Iodinolysis: 0.78 mmol of 4-iodobenzaldehyde per gram of polymer
IR (DRIFT, solid): 1707 cm$^{-1}$ C=O, 2715 cm$^{-1}$ CHO (weak)

EXAMPLE 7

Poly-(3-{dibutyl[2-(3-and-4-vinylphenyl)ethyl] stannyl}benzoic acid)-co-divinylbenzene (14)

The polymer-bound aldehyde 12 (190 mg, ~0.1 mmol of aldehyde), was added to a vial containing a solution of m-chloroperbenzoic acid (210 mg, 1.2 mmol) in 5 mL of methanol. After shaking for 25 h at RT, the solid was filtered and washed successively with 1 M NaOH, acetone, 1.7 M AcOH/ethanol, water, methanol/water/acetone, and methanol to afford 150 mg of 14.

Iodinolysis: 0.33 mmol of 3-iodobenzoic acid per gram of polymer. $^{119}$Sn MAS NMR: −39.3 ppm.

EXAMPLE 8

Poly-(4-{dibutyl[2-(3-and 4-vinylphenyl)ethyl] stannyl}benzoic acid)-co-divinylbenzene (15)

980 mg of the polymer-bound aldehyde 13 was added to 1.44 g (8.3 mmol) of m-chloroperbenzoic acid in 20 mL of methanol. After shaking for 18 h at RT, the solid was filtered and washed with 1M NaOH/ethanol, 12 mM HCl/ethanol, ethanol/methanol/water/acetone, methanol to yield 980 mg of the acid bound polymer 15.

IR (DRIFT, solid): 1695 cm$^{-1}$ C=O
Iodinolysis: 0.66 mmol of 4-iodobenzoic acid per gram of polymer

EXAMPLE 9

Poly-(4-{dibutyl[2-(3-and 4-vinylphenyl)ethyl] stannyl}hippuric acid)-co-divinylbenzene (16)

Into a 50 mL round-bottom flask, 44 mg (0.35 mmol) of glycine methyl ester hydrochloride, 45 mg (0.35 mmol) of diisopropylethylamine and 5 mL of dichloromethane were added and the mixture was stirred for few minutes to allow dissolution. To this was added 72 mg (0.35 mmol) of dicyclohexylcarbodiimide (DCC), 53 mg (0.34 mmol) of 1-hydroxybenzotriazide (1-HOBT) and 250 mg (~0.17mmol) of the polymer-bound benzoic acid 15. After stirring under a flow of argon for 5 days, at RT, the solid was filtered and washed with methanol/acetone, dicholoromethane, and methanol.

The ester group was hydrolyzed at reflux in 10 mL THF/water (1:1) in the presence of NaOH (400 mg, 10 mmol) for 4 h. The solid was filtered and washed with 1 M HCl, water, methanol/water/acetone, methanol/acetone, methanol to yield 180 mg of the benzamide bound polymer 16.

Iodinolysis: 0.58 mmol of 4-iodohippuric acid per gram of polymer

EXAMPLE 10

Poly-(4-{dibutyl[2-(3-and 4-vinylphenyl)ethyl]stannyl} N,N-diethylethylenediamino benzamidyl)-co-divinylbenzene (17)

Into a 50 mL round-bottom flask were placed 28 mg (0.2 mmol) of diethylethylenediamine, 27 mg (0.2 mmol) of collidine, 61 mg (0.3 mmol) of dicyclohexylcarbodiimide (DCC), 32 mg (0.2 mmol) of 1-hydroxybenzotriazide (1-HOBT), 150 mg (~0.1 mmol) of the polymer-bound benzoic acid 15 and 5 mL of dichloromethane. After stirring under a flow of argon for 7 days, at RT, the solid was filtered and washed with methanol/acetone, dicholoromethane, and methanol to yield 150 mg of the benzamide bound polymer 17.

Iodinolysis: 0.35 mmol of N-(2-(diethylamino)ethyl)benzamide and 0.08 mmol of 4-iodobenzoic acid per gram of polymer

EXAMPLE 11

Poly-(4-{dibutyl[2-(3-and 4-vinylphenyl)ethyl] stannyl}N-succinimidyl ester)-co-divinylbenzene (18)

Into a 50-mL round-bottom flask were placed 60 mg (0.3 mmol) of 1-(3-dimethylamino) propyl-3-ethylcarbodiimide hydrochloride (EDC), 35 mg (0.3 mmol) of N-hydroxysuccinimide (NHS), 52 mg (0.4 mmol) of collidine, and 7 mL of dichloromethane. This was stirred for 10 min. for complete dissolution. Then 50 mg (0.03 mmol) of the p-benzoic acid polymer 15 was added followed by stirring at RT for 70 h. The polymer was filtered and washed with methanol and acetone several times, to yield 46 mg of the activated ester polymer 18.

IR (DRIFT, solid): 1773 cm$^{-1}$, 1743 cm$^{-1}$ C=O

EXAMPLE 12

Poly-(4-{dibutyl[2-(3-and 4-vinylphenyl)ethyl] stannyl}N,N-diethylethylenediamino benzamidyl)-co-divinylbenzene (17)

Into a 25 mL vial were placed 32 mg of the polymer-bound activated ester 18, 31 mg (0.2 mmol) of diisopropylethylamine (DIPEA) and 37 mg (0.3 mmol) of N,N-diethylethylenediamine. After addition of 2 mL of dichloromethane, the reaction was allowed to stir for 23 h at RT. The solid was filtered and washed with methanol, water, methanol/water/acetone, and methanol to yield 27 mg of the benzamide bound polymer 17. Iodinolysis: 0.43 mmol of the N-(2-(diethylamino)ethyl)benzamide and 0.09 mmol of the 4-iodobenzoic acid per gram of polymer.

EXAMPLE 13

Synthesis of Benzofuran Precursor

Figure 7:
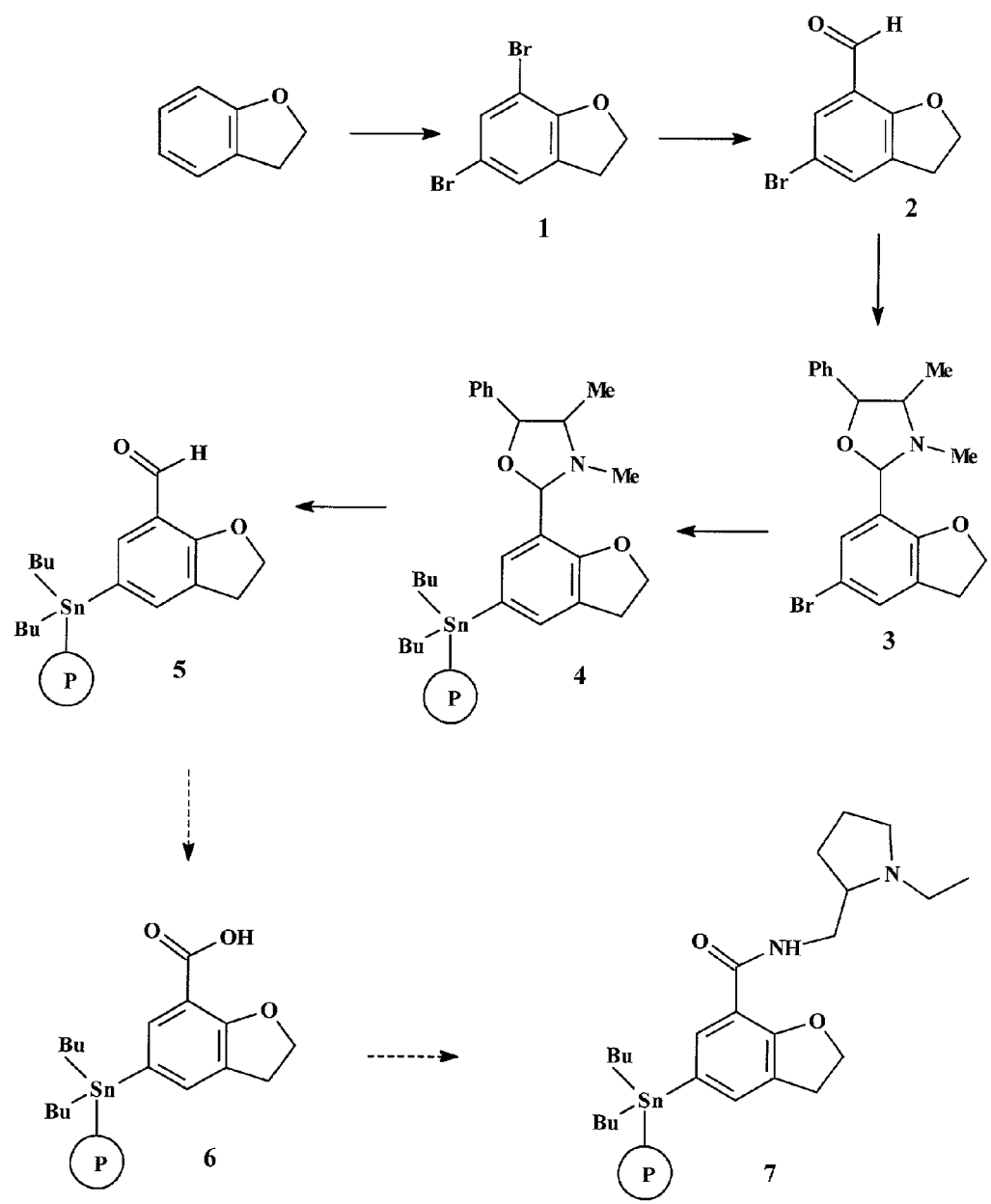
FIG. 7 depicts a route for the synthesis of certain compounds of the present invention (See Examples 13–19).

See FIG. 7 Route Q for synthetic route.

EXAMPLE 14

5,7-Dibromo-2,3-dihydrobenzofuran (19)

Bromine (13.0 mL, 250 mmol) in glacial acetic acid (50 mL) was added dropwise to 2, 3-dihydrobenzofuran (10 g, 84 mmol) in glacial acetic acid (100 mL) at 0° C. The reaction was allowed to come to room temperature and stirred overnight. Excess bromine was then destroyed by addition of sodium thiosulphate (150 mL 10% solution). After evaporation of the majority of the acetic acid, the residue was taken up in dichloromethane (150 mL) and washed with saturated sodium bicarbonate (3×50 mL), water (50 mL) and dried over anhydrous sodium sulfate. Solvent removal yielded an orange oil (18.8 g) which on distillation (0.015 mm Hg, 90° C.) gave 13.2 g (72%) of the desired product.

$^1$H NMR spectrum (CDCl$_3$) ppm: 7.37 (1H, s), 7.20 (1H, s), 4.65 (2H, t) 3.29 (2H, t). $^{13}$C NMR spectrum (CDCl$_3$) ppm: 157.0 (C8), 133.3 (C6), 130.4 (C4), 127.2 (C3), 112.5 (C7), 103.3 (C5), 72.1 (C2), and 30.8 (C1)

EXAMPLE 15

5-Bromo-2,3-dihydrobenzofuran-7-carbaldehyde (20)

A sample of 19 (6.0 g, 26.5 mmol) in freshly distilled dry THF was degassed at −78° C. and n-butyllithium (25 mL of 1.05 M, 26 mmol) was added dropwise by syringe. Then N,N-dimethylformamide (2.9 mL, 26 mmol) was added dropwise via syringe. The reaction mixture was allowed to come to room temperature overnight. Saturated ammonium chloride (10 mL) was added to and the mixture was stirred for 30 minutes. The solvent was removed and the residue was taken up in dichloromethane (50 mL), and washed with water (3×50 mL) then dried with anhydrous sodium sulfate. Solvent removal yielded yellow crystals (1.6 g) which were washed with ether and recrystallized from a minimum of hot methanol to give white crystals of 20 (1.32 g, 22%) mp=99–100° C.

$^1$H NMR (CDCl$_3$) (ppm): 10.10 (1H, s), 7.68 (1H, s), 7.47 (1H, s), 4.74 (2H, t), 3.24 (2H,t). $^{13}$C NMR (CDCl$_3$) (ppm): 187.7, 161.7, 133.8, 132.4, 129.6, 120.6, 112.9, 73.4, 28.7 Mass Spectrum: observed, 225.9629 amu, calculated 225.9629 amu.

EXAMPLE 16

(4S, 5S)-2-(5-bromo-2,3-dihydrobenzofuran-7-yl)-3, 4-dimethyl-5-phenyl-1, 3-oxazolidine (21)

A sample of 20 (650 mg, 2.9 mmol) and (1S, 2S) pseudoephedrine (500 mg, 3.0 mmol) in 40 mL of benzene was refluxed overnight using a Dean-Stark trap. Solvent removal yielded yellow crystals which were recrystallized from a minimum of hot hexanes to give white crystals of 21 (841 mg, 79%),mp=83.5–85.5° C.

$^1$H NMR spectrum (CDCl$_3$) ppm: 7.47 (1H, s), 7.27 (6H, m), 5.19 (1H, s), 4.66 (1H, d) 4.55 (2H, d), 3.13 (2H, t), 2.45 (1H d of q), 2.18 (3H, s), 1.14 (3H, s). $^{13}$C NMR spectrum (CDCl$_3$) ppm: 93.3, 86.6, 72.1, 69.1, 35.7, 29.7, 14.4. Mass Spectrum: observed 373.0672 amu, calculated 373.0672 amu.

EXAMPLE 17

Poly-(4S, 5S)-2-(5-{dibutyl[2-(4-vinylphenyl)ethyl] stannyl}-2,3-dihydrobenzofuran-7-yl)-3,4-dimethyl-5-phenyl-1,3-oxazolidine-co-divinylbenzene (22)

The previously prepared 21 (700 mg, 1.88 mmol), was added into a three-necked 200 mL round-bottom flask, equipped with a T-bore stopcock, a rubber septum and a powder addition side arm containing 850 mg of chlorostannane polymer (1.47 mmol SnCl/g of polymer). Under a flow of argon, 45 mL of freshly distilled dry THF was added by syringe. The flask and its contents were outgased three times at dry ice/acetone temperatures and an argon atmosphere was introduced. To the solution of 3 in THF at −78° C., n-butyllithium (0.75 mL, 1.88 mmol, 2.5 M) was added dropwise with the resultant formation of a yellow color. After 2 h at −78° C., the polymer was tipped into the THF solution, and the suspension was allowed to stir for 18 h and warm slowly to RT. To the suspension, about 5 mL of methanol was added and the suspension was filtered. The solid was washed with methanol, water, methanol/water/acetone, methanol/acetone and methanol several times to yield 1.6 g of 22.

$^{119}$Sn MAS NMR (ppm): −39.3, IR (DRIFT, cm$^{-1}$): 1014, 1061

EXAMPLE 18

Poly-5-{dibutyl[2-(4-vinylphenyl)ethyl]stannyl}-2, 3-dihydrobenzofuran-7-carbaldehyde-co-divinylbenzene (23)

To a sample of 22 (0.975 g) in a 5 dram sample vial, acetic acid (5 mL), methanol (5 mL), and water (1.3 mL) were added and the reaction was stirred for four hours and filtered. The insoluble material was washed with methanol, water, and acetone and dried under vacuum for 2 hours to yield 558 mg of a light yellow solid.

$^{119}$Sn MAS NMR (ppm): −39.2 IR (DRIFTS (cm$^{-1}$): 1686, 1648

EXAMPLE 19

Poly-5-{Dibutyl[2-(4-vinylphenyl)ethyl]stannyl}-2, 3-dihydrobenzofuran-7-carboxylic acid-co-divinylbenzene (24)

To 3-chloroperbenzoic acid (24.6 mg, 0.17 mmol) in a 5 dram sample vial in 7 ml of MeOH, a sample of 5 (82.5 mg) was added. The suspension was stirred for 1 h and then filtered. The precipitate was washed with methanol, water, and acetone and dried under vacuum for two hours to yield 74.3 mg of a light yellow material.

$^{119}$Sn NMR (ppm): 38.2 IR (DRIFTS, cm$^{-1}$): 1686

EXAMPLE 20

Benzamide Library

The following library of benzamides was produced using a procedure similar to Example 10:

| Amine | Iodinolysis mmol/g of polymer | | $^{119}$Sn NMR (ppm) | IR (cm$^{-1}$) C=O stretch |
|---|---|---|---|---|
| | 4-iodo-benzamide | 4-iodo-benzoic Acid | | |
| N,N-Dimethylethylene-diamine | — | — | −41.2 | 1658 |
| N,N-Diethylethylene-diamine | 0.40 | 0.10 | −41.2 | 1653 |
| N,N-Diisopropylethylene-diamine | 0.35 | 0.20 | −41.4 | — |
| N,N-Di-n-butylethylene-diamine | — | — | −41.2 | — |
| 1-(2-aminoethyl)-pyrrolidine | 0.32 | 0.29 | −41.2 | 1658 |
| 1-(2-aminoethyl)-piperidine | 0.41 | 0.17 | −41.2 | 1653 |
| 4-(2-aminoethyl)-morpholine | 0.54 | 0.11 | −41.1 | 1643 |

EXAMPLE 21

Purification of Benzamides from Iodinolysis

To approximately 4 mg of poly-(4-{dibutyl[2-(3-and 4-vinylphenyl)ethyl]stannyl}4-(2-aminoethyl)morphobenzamidyl)-co-divinylbenzene in a 25 mL vial was added ~2 mL of CH$_3$CN and ~1 mL of 0.1M I$_2$/CH$_3$CN. After shaking this suspension for 2 h, sufficient 0.2 M sodium thiosulfate was added to discharge the iodine colour. The resultant reaction mixture was then diluted four fold using equal volumes of methanol and 1M NaOH. About 2 mL of this solution was passed through a reverse phase C-18 SepPak (Adsorbex RP-18 (100 mg)). An HPLC analysis of this solution showed one peak consistent with 4-iodobenzaldehyde. The C-18 SepPak column was then washed with about 2 mL of water. HPLC trace of this solution showed one peak, 4-iodobenzoic acid. A wash with about 2 mL of ethanol produced a solution which upon HPLC analysis showed one peak, 4-iodo-N-(2-morpholin-4-ylethyl)benzamide.

EXAMPLE 22

The purification procedure was also applied as in Example 23 to the purification of N-[2-(diisopropylamino)ethyl]-4-iodobenzamide, 4-iodo-N-(2-pyrrolidin-1-ylethyl)benzamide and 4-iodo-N-(2-piperidin-1-ylethyl)benzamide. This procedure takes about 5–10 min.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

PATENTS AND PATENT APPLICATIONS

U.S. Pat. Nos. 6,015,544, 5,746,997, 5,720,935, 5,750,089, 5,609,848, 5,565,185, 5,424,402, 5,154,913, 4,980,467, 4,885,153, 4,430,319

PCT applications WO 9918053, WO 9818499

EQUIVALENTS

Those skilled in the art will recognize, or be able to recognize using no more than routine experimentation, many equivalents to the specific embodiments of the invention described herein. Such equivalents are intended to be encompassed by the following claims.

What is claimed:

1. A compound selected from the group consisting of: Poly-(4S, 5S)-2-(5-{dibutyl[2-(4-vinylphenyl)ethyl]stannyl}-2, 3-dihydrobenzofuran-7-yl)-3, 4-dimethyl-5-phenyl-1, 3-oxazolidine-co-divinylbenzene; Poly-5-{dibutyl[2-(4-vinylphenyl)ethyl]stannyl}-2, 3-dihydrobenzofuran-7-carbaldehyde-co-divinylbenzene; and Poly-5-{Dibutyl[2-(4-vinylphenyl)ethyl]stannyl}-2, 3-dihydrobenzofuran-7-carboxylic acid-co-divinylbenzene.

* * * * *